US006974439B1

(12) United States Patent
McKendry (10) Patent No.: US 6,974,439 B1
(45) Date of Patent: *Dec. 13, 2005

(54) APPARATUS FOR EXPRESSING MILK (75) Inventor: Bruce McKendry, Benicia, CA (US)

(73) Assignee: L. Jason Clute, Alamo, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 09/715,990

(22) Filed: Nov. 17, 2000

Related U.S. Application Data (63) Continuation-in-part of application No. 09/591,981, filed on Jun. 12, 2000.

(60) Provisional application No. 60/140,902, filed on Jun. 23, 1999.

(51) Int. Cl.[7] .............................. A61M 1/06; A01J 5/04

(52) U.S. Cl. ............................ 604/74; 604/75; 604/76; 119/14

(58) Field of Search ................................ 604/320, 315, 604/75, 74–80, 346; 422/101; 119/14.02, 119/14; 417/415, 411; 251/208; 601/14; 600/573

(56) References Cited

U.S. PATENT DOCUMENTS

| 4,263,912 A | | 4/1981 | Adams ...................... 128/281 |
| 4,607,596 A | * | 8/1986 | Whittlestone et al. ... 119/14.02 |
| 4,772,262 A | | 9/1988 | Grant et al. .................. 604/74 |
| 4,892,517 A | | 1/1990 | Yuan et al. ................... 604/74 |
| 5,070,403 A | * | 12/1991 | Wilkinson .................. 348/441 |
| 5,071,403 A | | 12/1991 | Larsson ....................... 604/74 |
| 5,233,996 A | * | 8/1993 | Coleman et al. ............ 600/529 |
| 5,358,476 A | * | 10/1994 | Wilson ......................... 604/74 |
| 5,514,166 A | * | 5/1996 | Silver et al. .................. 604/74 |
| 5,542,921 A | * | 8/1996 | Meyers et al. .............. 604/315 |
| 5,749,850 A | * | 5/1998 | Williams et al. ............ 604/320 |
| 5,776,098 A | | 7/1998 | Silver et al. ................. 604/74 |
| 6,287,521 B1 | * | 9/2001 | Quay et al. ................. 422/101 |
| 6,290,671 B1 | | 9/2001 | Niederberger ............... 604/74 |

* cited by examiner

Primary Examiner—Nicholas D. Lucchesi
Assistant Examiner—Roz Maiorino
(74) Attorney, Agent, or Firm—Greer, Burns & Crain, Ltd.

(57) ABSTRACT

A device for expressing milk from one or more breasts has at least one, and preferably two expressors and a pump. The expressors each have a cup for fitting on the breasts and a cup outlet to which a vacuum created by the pump can be connected. A filter that is substantially permeable to air but substantially impermeable to milk and water prevents milk from entering the vacuum pump. The filter is preferably permeable to air even when wet, though, so that the device can still be operated, even as the filter collects fluid.

5 Claims, 8 Drawing Sheets

APPARATUS FOR EXPRESSING MILK

This is a continuation-in-part of non-provisional application Ser. No. 09/591,981, filed Jun. 12, 2000, which is a of provisional application Ser. No. 60/140,902 filed Jun. 23, 1999.

FIELD OF THE INVENTION

This invention relates to apparatus for extracting natural milk, and more particularly, to breast pumps which are convenient and comfortable to use.

BACKGROUND OF THE INVENTION

Pumps for expressing milk from breasts are well-known. One known breast pump is disclosed in Whittlestone U.S. Pat. No. 4,607,596.

The Whittlestone patent discloses a breast pump having two milk collectors connected to a pump which applies both a vacuum and pulsating pressure to the breasts to extract milk. The pulsating pressure massages the breast to stimulate milk production, and the vacuum secures the milk collectors to the breasts and helps draw the milk and collect it. However, the vacuum at the two collectors can only be adjusted at the pump, and cannot be individually adjusted. This can create discomfort for the user if one breast is more sensitive than the other, or responds to stimulation differently than the other. Thus, there is a need for breast pumps having individual control of two collectors, which is more comfortable for the user.

The Whittlestone patent does not disclose a vacuum release for the collectors. As a result, when the device is turned off, the vacuum is broken by pulling the collectors from the breasts, or waiting for the vacuum to dissipate in order to remove the collectors. This is inconvenient and sometimes uncomfortable. Thus, there is a need for breast pumps having a vacuum release, preferably in a convenient location such as the collectors themselves.

In the Whittlestone device, milk from the two collectors is commonly drawn into a first collection vessel, and then a second collection vessel. The milk is drawn through vacuum lines, though, which makes cleaning difficult. Moreover, the milk collecting vessels are reusable, and require frequent and thorough cleaning. Accordingly, there is a need for breast pumps which are more sanitary and easier to clean than the Whittlestone device.

The Whittlesone patent discloses a breast cup having a housing, a relatively soft inner ring or donut, and a flexible liner. The liner wraps around the outlet of the cup, and a bung is inserted into the cup outlet to pass the vacuum and milk. At the inlet side, the liner is simply folded over the outside of the housing. This design has limitations. The liner is not accurately aligned and reliably sealed on the inlet side, so moisture and other contaminants can get inside the liner, which is undesirable. At the outlet, the liner can collapse around the entire breast, including the tip of the nipple, which can be uncomfortable and can cause unnecessary trauma. Accordingly, there is a need for breast pumps having cups which better fix the liner to the housing. There is also a need for breast pump cups which protect at least the end of the nipple from discomfort due to pulsating pressure.

The breast pump disclosed in the Whittlestone patent is a diaphragm pump operated by an electric motor. Rotation of the motor shaft is translated into back and forth action by a somewhat large and cumbersome linkage which moves the diaphragm. This adds not only size but weight to the pump, as well. This is a problem because storage and portability are desirable to breast pump users. Thus, there is a need for breast pumps which are lighter and smaller than known devices.

Accordingly, one object of this invention is to provide new and improved apparatus for extracting milk from breasts.

Another object is to provide new and improved breast pumps which are more convenient and comfortable to use.

Another object is to provide new and improved breast pumps having collectors with individual vacuum adjustments for each collector, and at least one vacuum release.

Still a further object is to provide new and improved breast pumps which are more sanitary, easy to clean and easy to disassemble and assemble.

Another object is to provide new and improved breast pumps which are more comfortable to use.

Yet another object is to provide new and improved breast pumps which are relatively light, compact and portable.

SUMMARY OF THE INVENTION

A device for expressing milk from one or both breasts has at least one milk collector and a pump. Preferably, the device has first and second collectors (also called expressors), so that both breasts can be milked simultaneously. Each expresser has a cup assembly which fits on the breast, a pulsation port to which a supply of pressurized pulsating air is connected, and a vacuum port to which a vacuum supply is connected. The pulsating air and vacuum are created by the pump. In use, pulsating air massages the breast and stimulates milk production, while the vacuum secures the collector on the breast and helps express the milk from the breast.

A vacuum adjustment is provided on each collector, and a vacuum release is provided on one, and preferably each collector. In this manner, the vacuum can be individually adjusted, and easily released.

The collectors also include a cap and manifold which direct the vacuum and pressure, a cup assembly which is preferably press fit onto the manifold, a collection vessel secured to the bottom of the manifold, and a one-way check valve or the like between the manifold and the collection vessel. After passing through the vacuum adjustment, the vacuum is directed through the cap and manifold, collection vessel and cup assembly so that the milk is drawn into the collector with little or no milk entering the vacuum lines to the pump. A filter may be provided for extra isolation of the vacuum pump and vacuum lines, if desired.

The cup assembly includes a bell housing, a relatively soft donut shaped pad, and a flexible liner, preferably made of silicone. The liner is secured to the inlet side of the cup assembly by a locking type of attachment, and extends around the bottom or lower end of the case, where it is secured by another locking press fit configuration.

The bottom end of the case fits into a receptacle in the manifold. The receptacle has a boss which extends into the cup assembly by a desired distance. This boss prevents the liner from collapsing around the end of the nipple during use.

The collector can be easily disassembled and cleaned in a dishwasher or the like, by removing the collection vessel and using or storing the milk, removing the cap and vacuum adjustment/release valve, and then removing the cup assembly. The cup assembly can be cleaned without removing the liner, if desired, or the liner can be removed and cleaned separately, or replaced. A cleaning cap can be placed over the air pulsation port of the cup assembly when the cup assembly is cleaned in its assembled condition, to prevent water from entering the space between the liner and the case.

The manifold, cap and valve can also be washed. The cup assembly can be easily reassembled after cleaning by reinserting the cup assembly in the manifold, re-attaching the cap to the manifold and cup assembly, and securing another collection vessel to the bottom of the manifold, with the check valve.

The pump includes a movable diaphragm in a chamber. The diaphragm is oscillated back and forth by a linear actuator motor such as a stepper motor. The motor preferably has a shaft which does not rotate, but moves back and forth axially. The shaft of the motor is directly or nearly directly linked to the diaphragm, which eliminates complex and cumbersome linkage components, reducing the size and weight of the pump.

BRIEF DESCRIPTION OF THE DRAWINGS

The above mentioned and other features of this invention and the manner of obtaining them will become more apparent, and the invention itself will be best understood with reference to the following description of an embodiment of the invention taken in conjunction with the accompanying drawings, in which.

DETAILED DESCRIPTION

Figure 1:
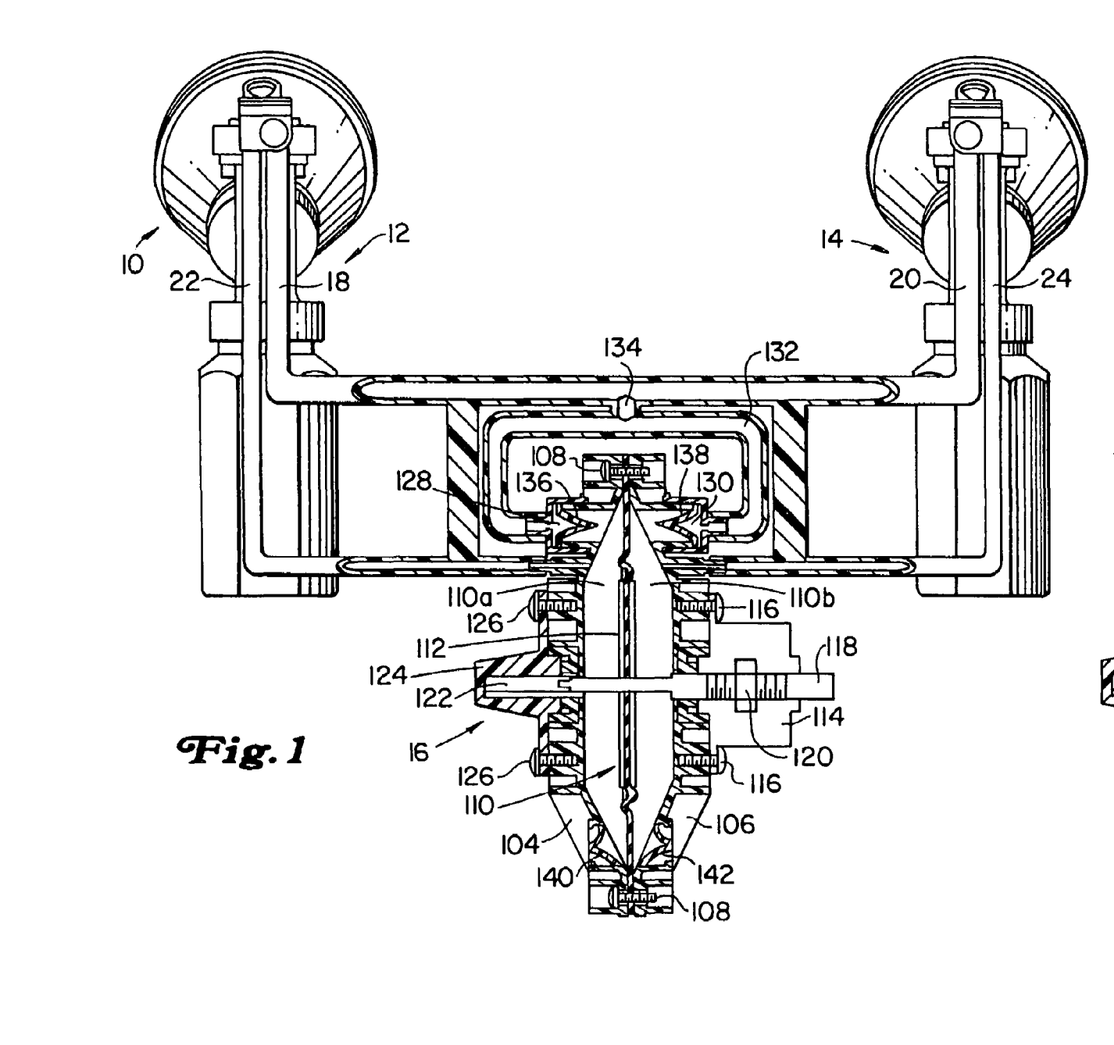
FIG. 1 is a partially cut-away perspective view of apparatus made in accordance with the principles of this invention.

Referring to FIG. 1, apparatus 10 is provided for expressing milk from one breast, or from two breasts simultaneously. The apparatus 10 includes a first collector or expressor 12 and a second expressor 14. A pump 16 is connected to both expressors 12, 14 through vacuum lines 18, 20, and air pressure lines 22, 24.

The pump 16 creates a vacuum which engages the breasts, and contributes to drawing the milk from the breasts. The pump also creates pressure pulsation around the areola and some or all of the nipple, as will be seen. The pump 16 can be powered by line voltage, a battery, manually or the like.

Figures 2, 3, 6:
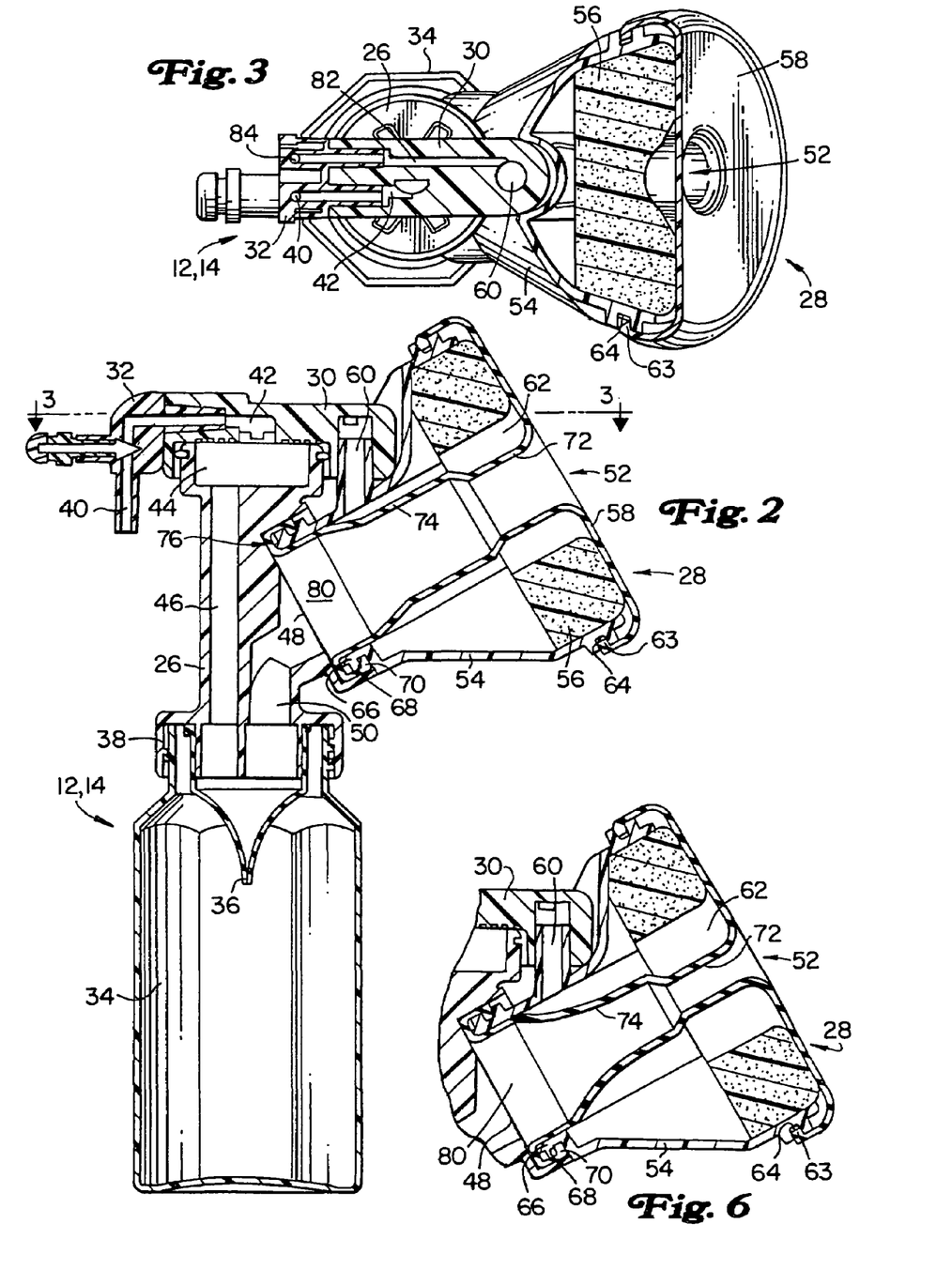
FIG. 2 is a milk collector used in the apparatus of FIG. 1, shown in cross-section.
FIG. 3 is a top view of the milk collector of FIG. 2, taken along lines 3—3 in FIG. 2.
FIG. 6 is a cut-away view of the collector of FIG. 2, showing the liner in a collapsed condition.

The expressors 12, 14 are shown in greater detail in FIGS. 2 and 3. Each expressor includes a manifold 26, a cup assembly 28 which fits over a breast, a cap 30, a filter 31, a vacuum adjustment release valve assembly 32, a sealing device 33 such as a wipe washer, o-ring or the like, a collection vessel 34 and a valve 36. The collection vessel can be a bottle made of plastic-like material or the like, or a bag, as will be seen, as can be oriented at an obtuse angle with respect to the cup assembly, as shown.

The manifold 26 includes an opening 38 which is preferably threaded, so that a collection vessel such as a plastic milk bottle can be threadedly secured to the manifold 26, with the valve 36. The valve 36 is preferably a one-way check valve such as a duck bill valve or the like.

A vacuum enters the expresser through a vacuum port 40 in the assembly 32. After passing through a port 42 in the cap 30, the vacuum enters a vacuum path in the manifold 26 through an opening 44 in the top of the manifold. The vacuum is drawn through an internal orifice 46 to the opening 38, which is beneath the port 42 and the cup assembly 28. The vacuum tends to close the valve 36, which prevents a substantial buildup of vacuum in the collection vessel 34.

The vacuum is drawn from the opening 38 to a cup assembly opening or milk outlet port 48 through a channel 50. When milk is drawn from the breast, the milk passes through the channel 50 under the force created by the vacuum, but most of the milk drops into the valve 36 through the force of gravity, and does not enter the orifice 46. When sufficient milk collects in the valve 36, the weight of the milk forces the valve open, which releases the milk into the collection vessel 34. In this manner, the milk is collected without contaminating the vacuum lines 18, 20 (FIG. 1).

The cup assembly 28 has an milk inlet port 52 in addition to the outlet port 48. The components of the cup assembly 28 include a bell housing 54, a donut shaped pad 56, and a flexible liner 58, shown disassembled in FIG. 4. The cup assembly 28 also has an air pressure pulsation port 60 which allows air to enter a space 62 between the case bell housing 54 and the liner 58.

Figures 4, 7:
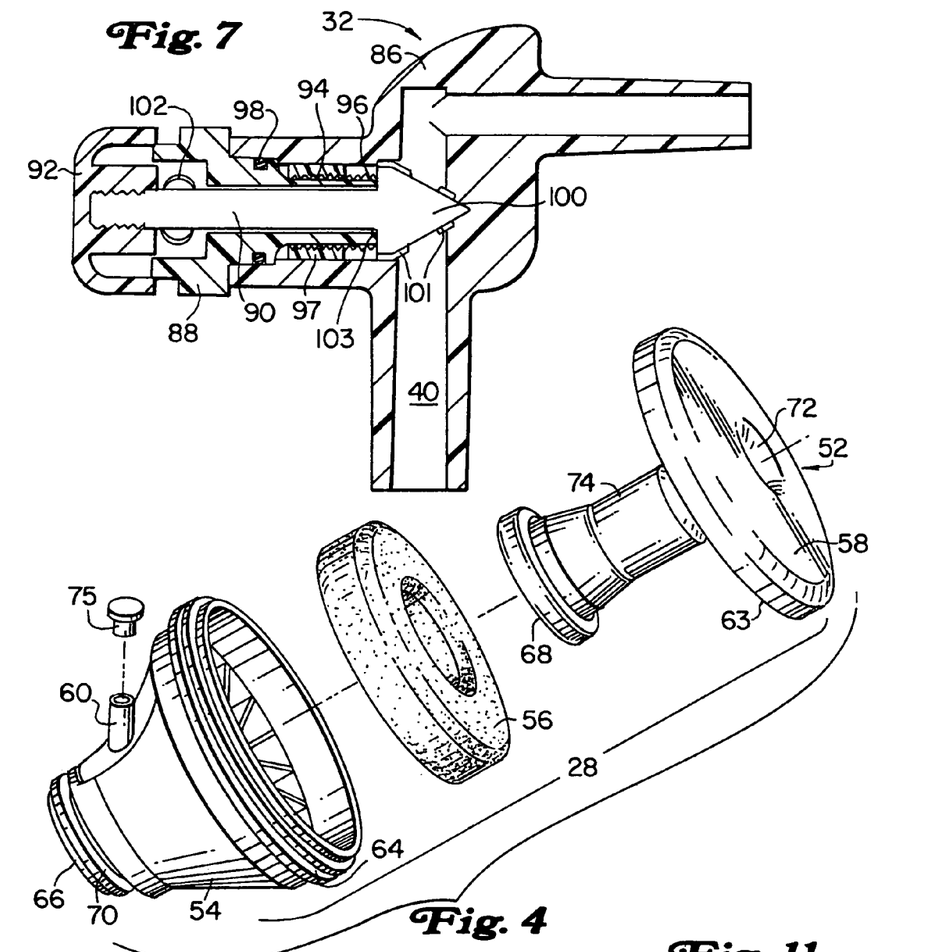
FIG. 4 is an exploded view of a cup assembly used in the collector of FIG. 2.
FIG. 7 is a cut-away view of a vacuum adjustment/release assembly in the collector of FIG. 2.

The cup assembly 28 is assembled by placing the donut shaped pad 56 in the housing 54 as shown, and does not need further securement. The pad 56 is preferably made of a suitable foam material which is sized to fit snugly in the housing 54. However, the pad 56 can be easily removed by placing a finger through the opening in the ring and pulling the ring out.

The liner 58 is installed in the cup assembly 28 by securing an end 63 to the liner 58 in a groove 64 formed in the housing 54 (FIGS. 2, 3 and 4). The end 63 and groove 64 are shaped to provide locking press fit type of securement.

The liner 58 extends from the groove 64 over and around the pad 56 and inside of the housing 54 to a bottom end 66 of the housing 54. An end 68 of the liner 58 is inserted into a groove 70 near the end 68 for securement in a press fit fashion. The liner 58 can be any suitable shape, including the shape shown in FIG. 2, which includes a relatively narrow section 72 near the inlet opening 52, and a wider section 74 between the section 72 and the outlet end 48 of the cup assembly 28. This shape places more pressure around the areola region of the breast, while placing less pressure on the nipple itself.

By sealing the liner to the case at both ends, the assembly can be washed without taking the liner off, if a cleaning cap 75 is placed over the pressure inlet 45 (FIG. 4).

Figure 5:
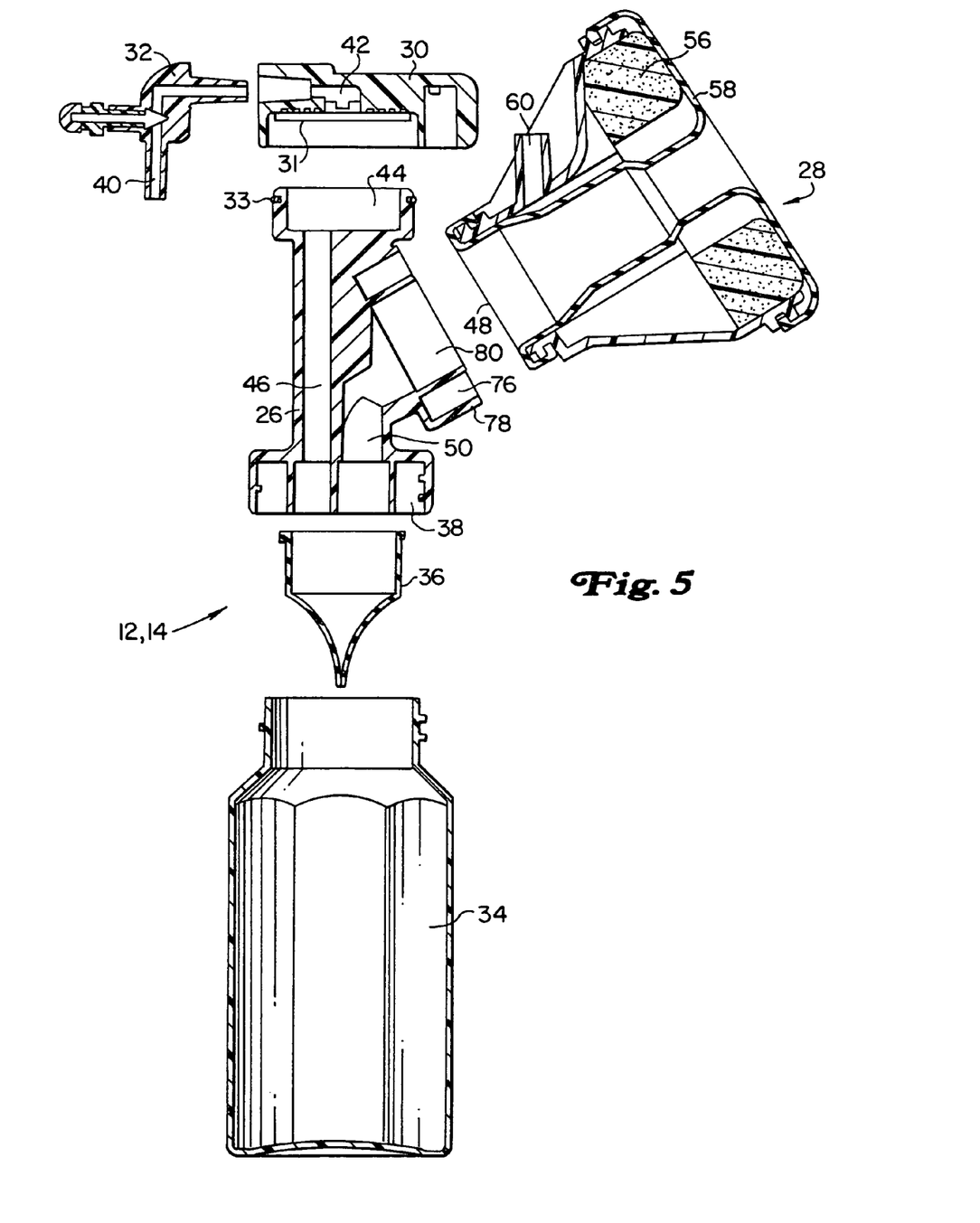
FIG. 5 is an exploded view of the collector of FIG. 2.

The cup assembly 28 can be press fit into a circular groove 76 in the manifold 26, seen in FIG. 5. The groove 76 is formed by an outside wall 78 and an inside boss 80. The boss 80 can extend outwardly as far as desired, and can be any suitable shape, such as circular, triangular, square, rectangular, elliptical, hexagonal, etc. Since the boss 80 is hollow and prevents the liner 43 from collapsing under outside air pressure, the boss 80 protects any part of the nipple which is inside the boss from pressure when the liner is collapsed, as seen in FIG. 6.

The cap 30 (FIGS. 2, 3 and 5) includes an air pressure/pulsation channel 82, which extends from an air pressure inlet 84 in the assembly 32 to the port 60. The cap can be press fit over the manifold opening 44 and the cup assembly air pressure/pulsation port 60, and can be easily removed. When installed, the cap 30 further secures the cup assembly in the manifold, but both the cap and the manifold can be removed without tools for cleaning purposes. The cap itself can be easily cleaned in a dishwasher or the like by removing the vacuum adjustment/release assembly 32, if desired, which is preferably press fit into the cap 30. The filter 31, if used, further prevents liquids or the like from entering the vacuum lines and the pump.

The filter 31 is preferably permeable to air flow when dry and also when wet, which can happen if milk contacts the filter. Thus, if the filter becomes wet due to milk and/or water, air can still pass through the filter because the filter remains permeable to air. An example of such a filter is Versapor R1200 (part no. 66393) by Pall Corp.

The vacuum adjustment assembly 32 includes a housing 86, a thumbwheel 88, a pin 90, and a cap 92, shown in FIG. 7. The thumbwheel 88 has threads 94 which adjustably secure the thumbwheel 88 in an orifice 96 in the housing 86. A threaded insert 97 can be secured in the orifice 96 for this purpose. An O-ring 98 maintains the vacuum in the line 40.

An end 100 of the pin 28 at least partially enters the vacuum port 40 to regulate the vacuum. The vacuum to the expressors is cut off when the end 100 is pressed against a valve seat 101.

The cap 92 is secured to the pin 90 by adhesive or the like. The pin 90 is preferably biased away from the port 40 by a spring 102, which presses the cap 92 away from the thumbwheel 88 and normally opens the vacuum port 40 when the pin 90 is released. The port 40 is opened to a desired extent by turning the thumbwheel 88 until a suitable vacuum level is set. A mylar or other suitable gasket 103 between the end 100 and the thumbwheel 88 prevents undesired loss of vacuum through the assembly 32.

The spring 102 allows the pin 90 to be pressed down so that it releases the vacuum in the cup assemblies 28 when the seal created by the gasket 103 is broken. The vacuum at both expressors 12, 14 can be released by pressing the vacuum release on one or both of the expressors.

Referring again to FIG. 1, the pump 16 has two halves 104, 106 secured together by screws or the like 108 to form a chamber 110. The screws 108 also secure a movable diaphragm 112 in place. The diaphragm 112 divides the chamber 110 into two halves 110a, 110b.

The diaphragm 112 is oscillated in a back and forth manner by a motor 114. The motor can be secured to the housing by bolts 116 or the like.

The motor 114 can be a stepper motor, which is one form of a linear actuator, which has a shaft 118. The shaft 118 moves in and out of the motor 114 in the axial direction without rotation. The shaft 118 is threaded, and is moved by a rotating threaded ring 120, which is similar to a nut. Rotation of the ring 120 moves the shaft 118 linearly. In this manner, the shaft 118 can move the diaphragm 112 back and forth essentially directly, without large, complex linkages.

The distal end of the shaft 118 can be guided by an opening 122 in an end cap 124. The end cap 124 is secured by bolts 126.

The pump 16 also has vacuum outlets 128, 130 in the chamber 110, on opposite sides of the diaphragm 112. The vacuum lines 18, 20 are connected to the vacuum outlets 128, 130 through a common vacuum line 132, which accesses the lines 18, 20 equally and simultaneously through a port 134. Check valves such as duck bill valves 136, 138 control the vacuum and pumping operation, and exhaust valves 140, 142 release the pressure created in the chamber halves 110a, 110b by the movement of the diaphragm 112. However, some of the pressure generated by the diaphragm is transmitted through the pressure lines 22, 24 to the collectors 12, 14. The pressure forces the liners 58 against the breasts (see FIG. 6), which further stimulates release of milk. While the vacuum is fairly continuous, though, the pressure pulsates. In fact, when the diaphragm moves away from a pressure line 22, 24, air is drawn out and a partial vacuum can be created.

Figure 8:
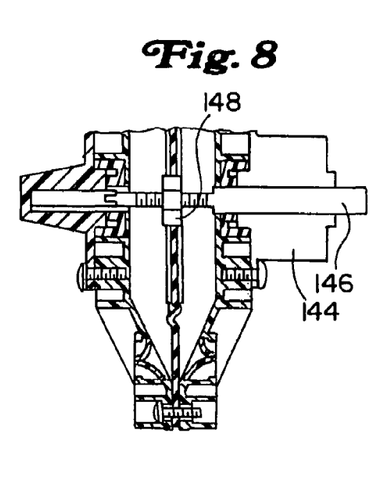
FIG. 8 is a cut-away view of an alternate embodiment of the pump used in the apparatus of FIG. 1.

The device is light weight, portable and compact because large motor linkages are eliminated. Wear is also reduced by simplifying the power train in this manner. The motor 114 can be any suitable device which creates a fairly self-contained drive system which is relatively small in size and fairly quiet. In fact, the motor can be an ordinary motor 114 with a threaded rotating shaft 146, as seen in FIG. 8. In that embodiment, a fixed ring 148 is attached to the diaphragm. The ring 148 is also threaded, so when the shaft 146 rotates forward and backwards, the diaphragm 112 moves back and forth.

Figure 9:
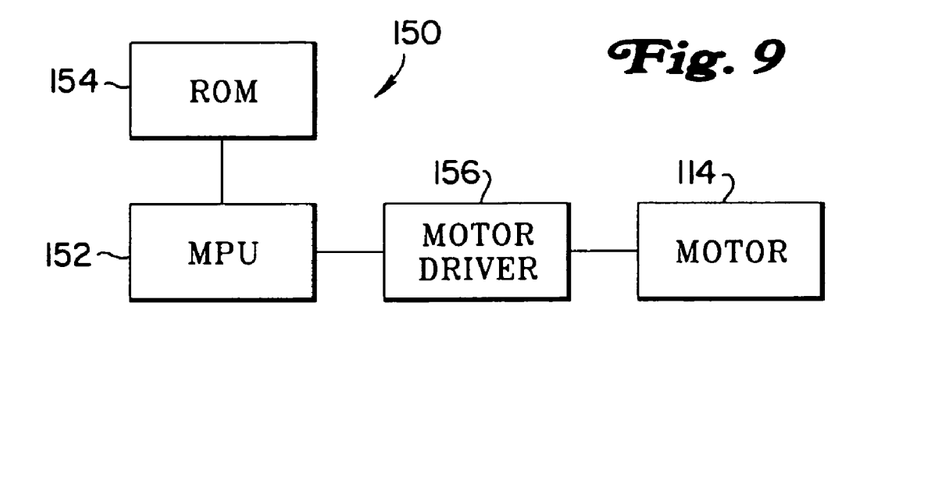
FIG. 9 is a block diagram of a control system for the apparatus of FIG. 1.

The motor can be controlled in any suitable manner, such as the control system 150 shown in FIG. 9. An application specific integrated circuit or the like has a microprocessor 152 and a ROM 154, programmed to cause a motor driver 156 to set the desired rate of rotation and the direction of rotation of the motor. The rotation rate, as well as the timing of the back and forth motion of the diaphragm, can be controlled in this manner.

Figure 10:
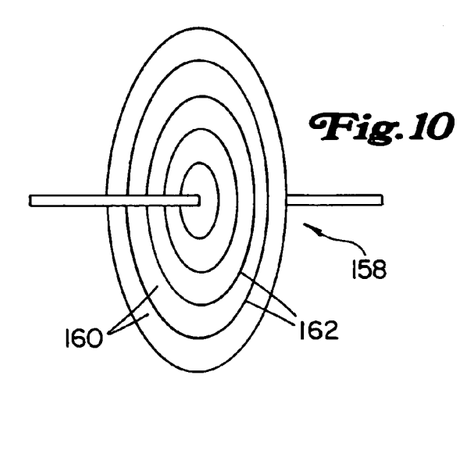
FIGS. 10 and 11 are diagrams of an alternate embodiment of the diaphragm used in the pump in the apparatus of FIG. 1.
Figure 11:
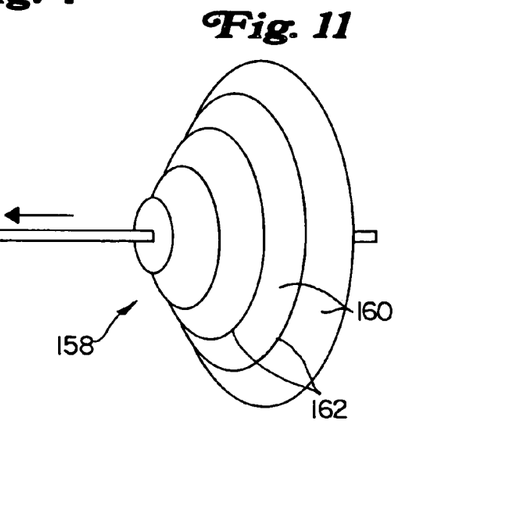

The diaphragm 112 can be any suitable configuration, such as that shown in FIG. 1, which features a flat stiff middle section flanked by soft corrugations. Another design is shown in FIGS. 10 and 11, where a diaphragm 158 has a plurality of rings 160 joined by corrugations 162.

Figure 12:
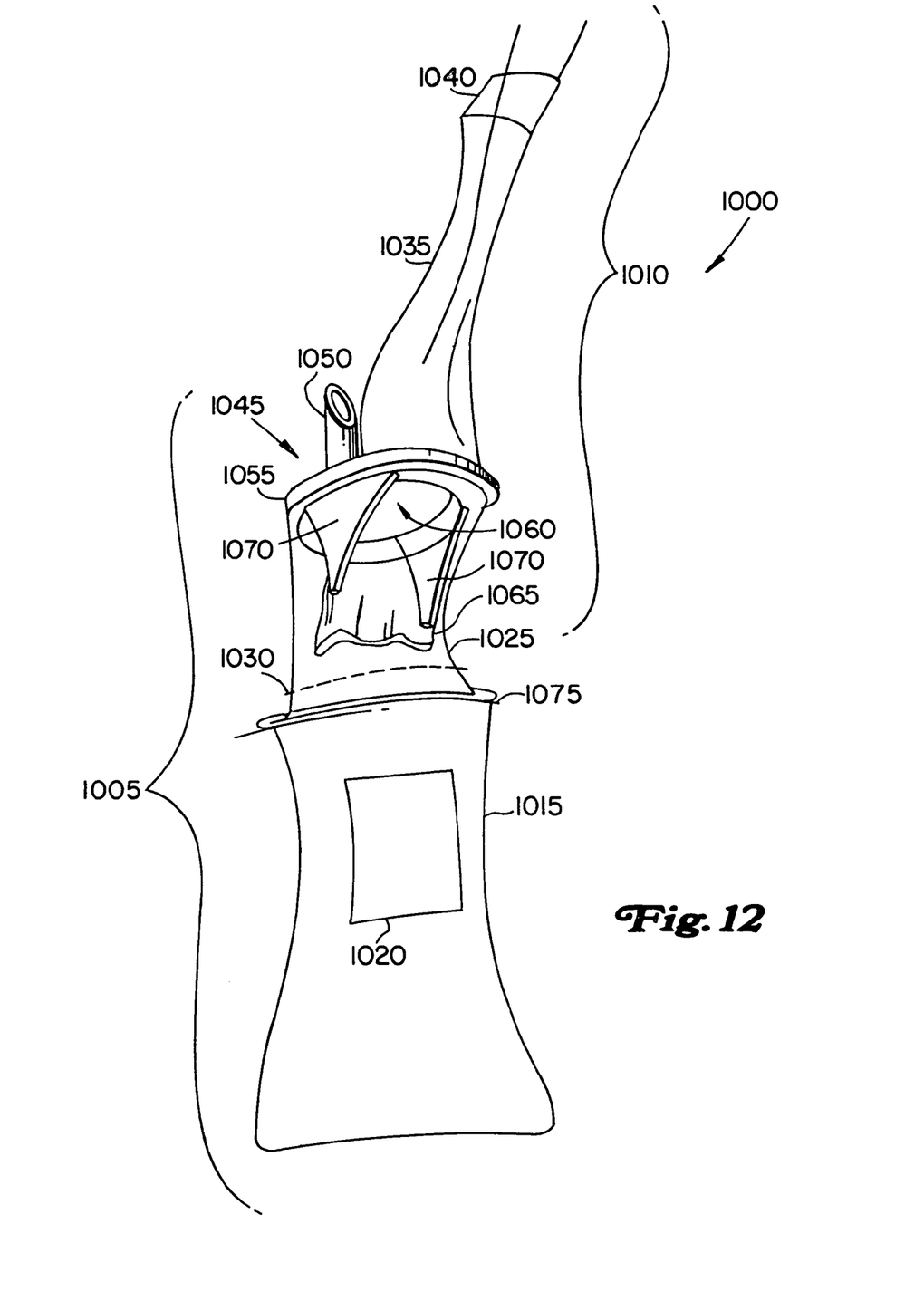
FIG. 12 is a perspective view of another embodiment of the collecting vessel of FIG. 2 as a flow-through bag.

FIG. 12 is a perspective view of another embodiment of a collection vessel as a flow-through bag 1000, which can be used to eliminate the need for sterilization of the unit as assembled in FIG. 2. The bag portion can be molded with a grain which facilitates easy removal. The flow-through bag 1000 includes a channel portion 1010 and a milk-collecting bag portion 1015. The channel portion 1010 includes a flexible neck 1035 defining an internal channel. The flexible neck 1035 is configured to be inserted into the milk outlet 38, through the vacuum/milk communication pipe 50, through the inside of the liner 58, and out the breast cup assembly 28. The channel portion 1010 preferably includes a breast cup overlay (1315, FIG. 15) similar to that of the lines 58 at the distal end of the neck 1035 to overlay the breast cup assembly 28 at the inlet 52. The breast cup overlay 1315 may be maintained over the breast cup assembly 28 using the locking mechanism previously described, a tie wire, rubber band or nothing. The upper portion (1320, FIG. 15) of the neck 1010 is preferably shaped similar to the flexible liner 58, so that no buckling of material occurs. The channel portion 1035 may include removable tape 1040 for clamping the neck 1035 and powder (not shown) to facilitate the feeding of the flexible neck 1035 through the manifold 26 and breast cup assembly 28.

A vacuum spout and one-way valve molding 1045 is sealed within the proximate end of the internal channel defined by the neck 1035. The molding 1045 effectively divides the internal channel into a first internal channel portion which is fed through the breast cup assembly 28 and a second internal channel portion which forms a skirt 1065 about the molding 1045.

Figure 13:
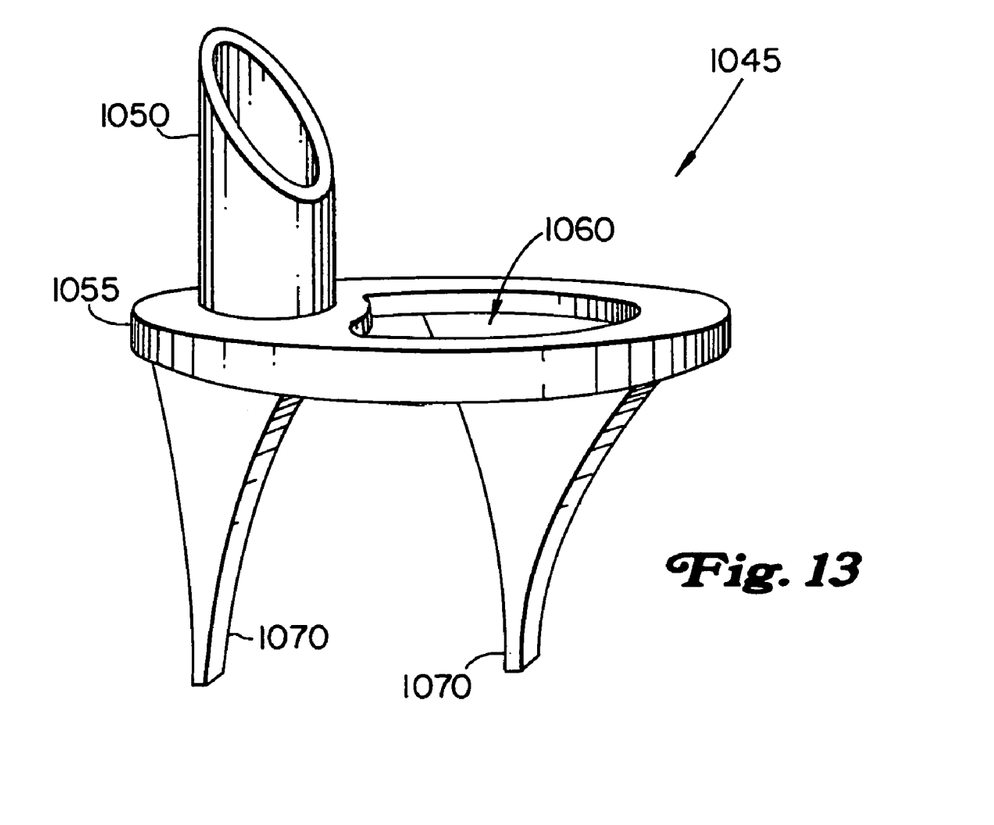
FIG. 13 is a perspective view of the annular ring of FIG. 12.

The vacuum spout and one-way valve molding 1045 is shown in greater detail in FIG. 13. The molding 1045 includes an annular ring 1055 sealed within the proximate end of the internal channel defined by the neck 1035. The annular ring 1055 forms a vacuum/milk passage (aperture) 1060 therethrough. The molding 1045 further includes a vacuum spout 1050 coupling the second internal channel portion to an environment external the neck 1035. The vacuum spout 1050 enables vacuum pressure from the vacuum pipe 46 to flow through the vacuum spout 1050, through the annular ring 1055, and back up the vacuum/milk passage 1060 to the breast cup assembly 28.

The molding 1045 also includes two rigid plastic prongs 1070 directed away from the neck 1035 for encouraging duckbill check valve action with the flexible skirt 1065 that overhangs the annular ring 1055. Accordingly, vacuum pressure exerted through the vacuum spout 1050 causes the flexible skirt 1065 to close about the two rigid prongs 1070. Milk can still flow down the internal channel defined by the neck 1035, through the vacuum/milk passage 1060, through the one-way valve 1065, and into the bag portion 1005. Alternatively, the molding 1045 can alternatively include a ball valve, a duck-bill check valve like valve 36, or any other one-way valve.

The bag portion 1005 includes a milk-collecting possibly disposable bag 1015, having a label area 1020 for a banner and/or note area for writing information such as date and time of expression. The bag portion 1005 preferably includes a bag sealing mechanism 1075 for enabling waterproof closure of the bag, and a water-and-air-tight grain 1030 for enabling easy removal of the disposable bag 1015. Alternatively, the bag 1015 can be cut with scissors. Although not shown in FIG. 12, a clamping mechanism (see FIG. 14) holds the annular ring 1055 within and against the milk-collecting bag 1015.

Figure 14:
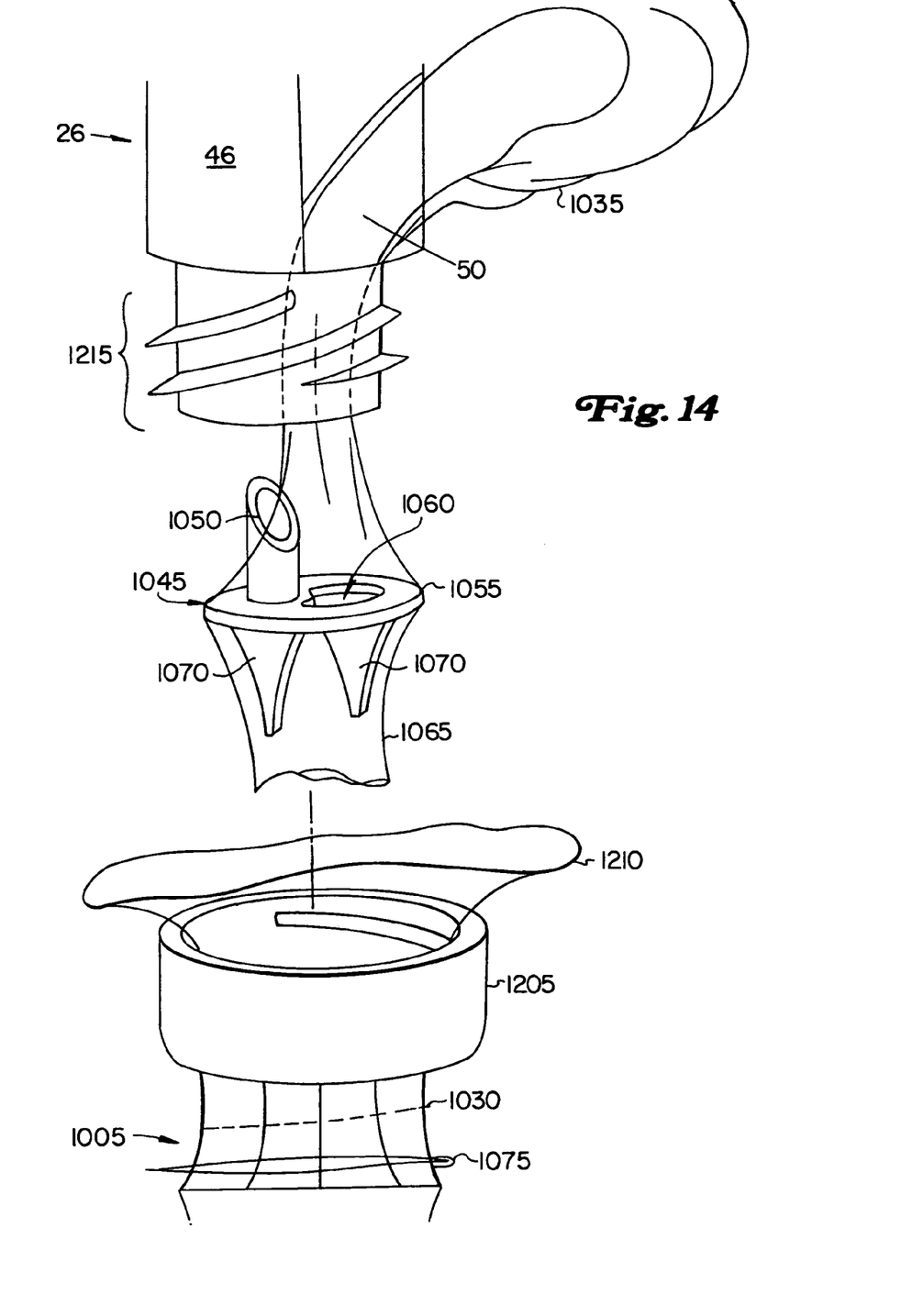
FIG. 14 is an exploded perspective view of the flow-through bag connection mechanism.

FIG. 14 is a perspective view of an example attachment for the flow-through bag 1000. As illustrated, the neck 1035 is inserted up the vacuum/milk communication pipe 50 of the manifold 26. The collecting vessel attachment mechanism, illustrated as threading 1215, is shown as dangling out of the manifold 26.

In the embodiment illustrated in FIG. 14, the top end 1210 of the disposable bag 1005 is inserted through a clamping mechanism 1205 and folded over. The clamping mechanism 1205 preferably includes threading (not shown) to engage the threading 1215 of the manifold 26. When the clamping mechanism 1205 is attached to the threading 1215, the vacuum spout 1050 preferably is directed up the vertical vacuum pipe 46, the annular ring 1055 abuts the edge of the threading 1215, and the molding 1045 forces the channel portion 1010 against the disposable bag 1005 thereby creating a waterproof seal and supporting the disposable bag 1005.

Figure 15:
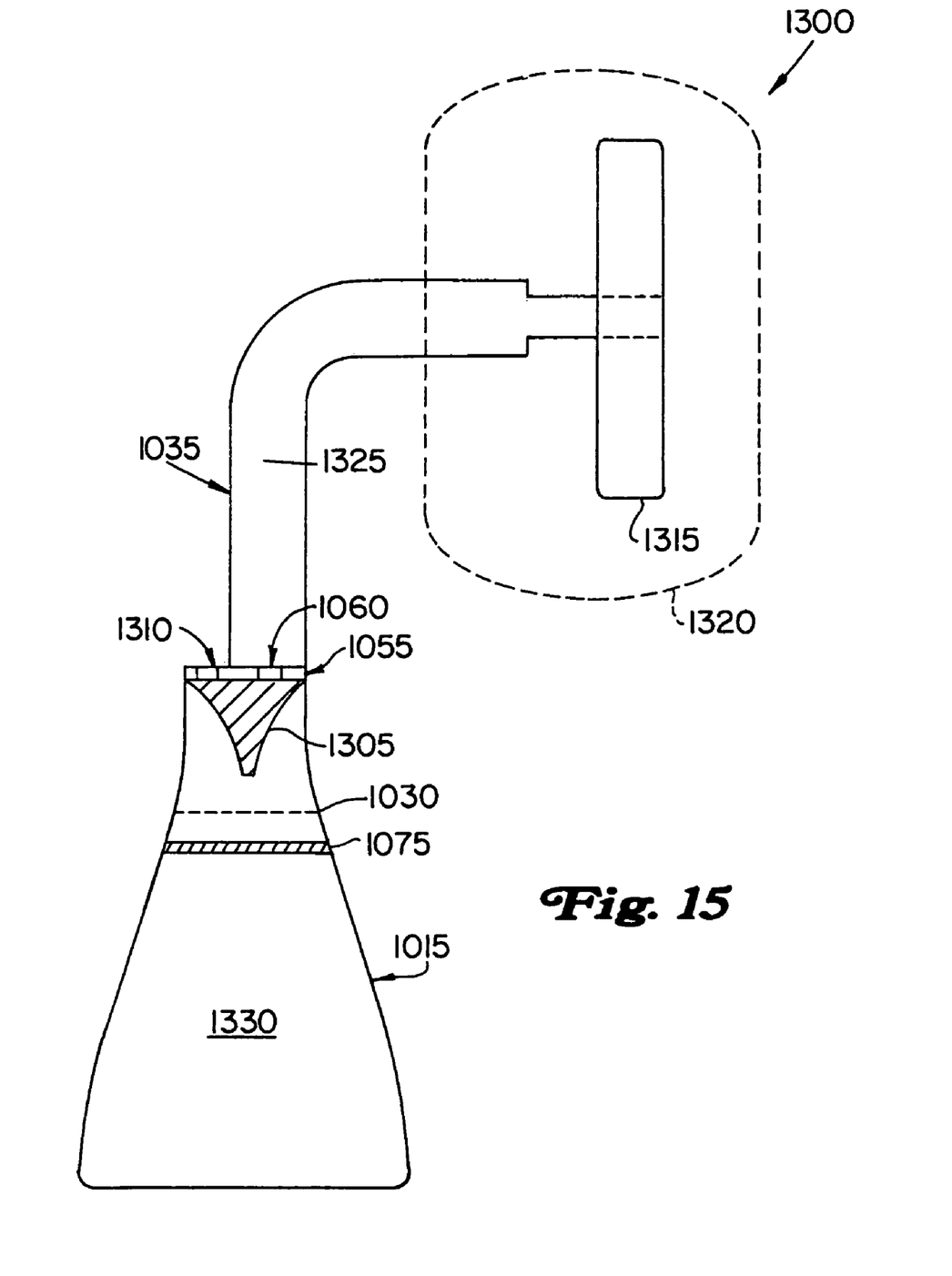
FIG. 15 is a cross-sectional side view of the flow-through bag as an integral unit.

FIG. 15 illustrates another embodiment as a integral bag, neck and molding unit 1300. As shown, the neck 1035 and bag 1015 are a single unit. The molding 1055 is sealed within the unit 1300 to form a vacuum/milk aperture 1060 dividing the internal channel into a neck channel portion 1325 and a bag channel portion 1330. The molding also includes a vacuum aperture 1310 from a point external the unit 1300 to the bag channel portion 1330. The molding 1055 also includes a one-way valve, illustrated as a duckbill check valve 1305. Although not shown, a connection mechanism is used to maintain the molding 1055 against the vertical vacuum tunnel 46 of the manifold 26, so that vacuum pressure can be exerted through the vacuum aperture 1310, through the vacuum/milk aperture 1060 and onto the breast. Because the bag is a single unit, the connection mechanism need not maintain a water-and-air-tight seal between the two bag portions of FIGS. 12–14.

In use, power is applied to the pump 16, and the expressors 12, 14 are placed over the breasts. The vacuum created by the pump 16 secures the expressors 12, 14 on the breasts and helps draw milk from the breasts. The pulsating air massages the breast to stimulate milk production, and reduces the amount of vacuum needed to collect the milk.

The vacuum in each expressor 12, 14 can be adjusted individually by turning the thumbwheels 88, without pressing pins 90 down. To release the vacuum, one or both of the pins 90 is pressed down. The device can be easily disassembled without tools, cleaned and reassembled.

The many advantages of this invention are now apparent. Breast pumping is more comfortable because the user can individually control the vacuum supplied to each breast. Release is also more comfortable because the vacuum can be released before removal. Cleaning is more convenient because milk does not enter the vacuum lines. Moreover, the entire collector can be easily disassembled for cleaning and reassembled without tools. The bosses in the expressors protect the end of the nipple from irritation, which is comfortable. Moreover, the entire pump is small, lightweight and relatively quiet.

While the principles of the invention have been described above in connection with a specific apparatus and applications, it is to be understood that this description is made only by way of example and not as a limitation on the scope of the invention. For example, various aspects of the invention could be used to milk animals, as well as humans.

What is claimed is:

1. A device for expressing milk from a breast comprising:
   a manifold having a vacuum path, said vacuum path having an inlet, an outlet and a midsection between said inlet and said outlet;
   a vacuum source connected to said inlet;
   a breast cup connected to said outlet and adapted for securement to the breast;
   a liner in said breast cup;
   a hollow boss in said manifold that extends partially into said breast cup adjacent said outlet, said hollow boss preventing a portion of said liner from collapsing under air pressure, and protecting part of the breast inside said hollow boss from pressure from said liner;
   a milk collector having a collector inlet operatively connected to said vacuum path; and
   a filter in said vacuum path between said vacuum source and said milk collector so as to prevent milk from contaminating said vacuum source without preventing milk from entering said milk collector, said filter being substantially permeable to air when said filter is either dry or wet, and substantially impermeable to liquid when said filter is either dry or wet.

2. A device for expressing milk from a breast comprising:

a manifold having a vacuum path, said vacuum path having an inlet, an outlet and a midsection between said inlet and said outlet, said midsection being beneath said inlet and said outlet in use;

a vacuum source connected to said inlet;

a breast cup connected to said outlet and adapted for securement to the breast;

a liner in said breast cup;

a hollow boss in said manifold that extends partially into said breast cup adjacent said outlet, said hollow boss preventing a portion of said liner from collapsing under air pressure, and protecting part of the breast inside said hollow boss from pressure from said liner;

a milk collector having a collector inlet operatively connected to said midsection of said vacuum path; and a filter in the vacuum path between said vacuum source and said milk collector so as to prevent milk from contaminating said vacuum source without preventing milk from entering said milk collector, said filter being substantially permeable to air when said filter is either dry or wet, and substantially impermeable to liquid when said filter is either dry or wet;

whereby milk which is drawn from the breast by said vacuum source falls into said milk collector by force of gravity and is substantially not drawn through said vacuum inlet.

3. Apparatus for expressing milk from a breast comprising a milk collector unit having a manifold, the manifold having a vacuum path and a pulsation pressure path;

a collection vessel operatively connected to said vacuum path, the vacuum path having an inlet, an outlet and a midsection between said inlet and said outlet, said inlet being connected to a vacuum source;

a cup assembly, said cup assembly having a housing having an inlet and an outlet, a pad located in said inlet of said housing, and a liner extending from said housing inlet to said housing outlet, said liner being secured to said housing to form a space between said housing and said liner which is in communication with said pulsation pressure path, pressure in said pulsation path moving said liner within said housing;

a hollow boss in said manifold that extends partially into said cup assembly housing inlet, said hollow boss preventing a portion of said liner from collapsing under air pressure, and protecting part of the breast inside said hollow boss from pressure from said liner;

a filter in the vacuum path between said vacuum source and said milk collector so as to prevent milk from contaminating said vacuum source without preventing milk from entering the milk collector, said filter being substantially permeable to air when said filter is dry or wet, and substantially impermeable to liquid when said filter is either dry or wet.

4. The apparatus of claim 3 wherein said manifold assembly includes a manifold to which said collection vessel is secured, and a removable cap, said cup assembly being secured to said manifold assembly by both said manifold and said cap.

5. The apparatus of claim 4 wherein said vacuum path begins in said cap and passes through said manifold to said cup assembly, and said pulsating pressure path passes through said cap to a pressure port in said cup assembly, said pressure port being in communication with said space between said housing and said liner.

* * * * *

UNITED STATES PATENT AND TRADEMARK OFFICE
CERTIFICATE OF CORRECTION

| | | |
|---|---|---|
| PATENT NO. | : 6,974,439 B1 | Page 1 of 1 |
| APPLICATION NO. | : 09/715990 | |
| DATED | : December 13, 2005 | |
| INVENTOR(S) | : Bruce McKendry | |

It is certified that error appears in the above-identified patent and that said Letters Patent is hereby corrected as shown below:

In the Specification:

Col. 1, line 4, delete "is a of" and insert --is a continuation-in-part of--.

Signed and Sealed this

Eighteenth Day of July, 2006

JON W. DUDAS
*Director of the United States Patent and Trademark Office*